United States Patent [19]

Uehara et al.

[11] Patent Number: 5,292,531

[45] Date of Patent: Mar. 8, 1994

[54] DERMATOLOGIAL EXTERNAL AGENT

[75] Inventors: Keiichi Uehara; Yoshihiro Ohhata, both of Yokohama; Akio Kawabata, Hyogo; Yoshikazu Inoue, Kakogawa; Yoshihiro Yokogawa, Yokohama; Yuji Tsutsumi, Tokyo, all of Japan

[73] Assignee: Shiseido Company Ltd., Tokyo, Japan

[21] Appl. No.: 761,855

[22] Filed: Sep. 12, 1991

[30] Foreign Application Priority Data

Jan. 19, 1990 [JP] Japan .................. 2-10023

[51] Int. Cl.⁵ .................. A61K 7/48
[52] U.S. Cl. .................. 424/40 L; 424/405
[58] Field of Search .......... 424/401, 405, 78.03, 424/78.07; 530/210, 211, 212; 524/270, 271, 272, 273, 274

[56] References Cited

U.S. PATENT DOCUMENTS 2,608,541  12/1948  Troyan et al. .................. 524/274

FOREIGN PATENT DOCUMENTS

| 2162464 | 7/1973 | France . | |
|---|---|---|---|
| 0018791 | 2/1976 | Japan | 524/274 |
| 63-183511 | 7/1988 | Japan | A61K 7/00 |
| 63-183512 | 7/1988 | Japan | A61K 7/00 |
| 63-183513 | 7/1988 | Japan | A61K 7/00 |
| 63-183514 | 7/1988 | Japan | A61K 7/00 |
| 2-188513 | 7/1990 | Japan | A61K 7/00 |
| 0588992 | 6/1947 | United Kingdom | 524/274 |

OTHER PUBLICATIONS

Yokogawa Yoshihiro et al., Skin Drug for External Use, vol. 459 (C–767), Oct. 4, 1990; & JP-A-02 188 513 (Shiseido) Jul. 24, 1990 Abstract.

Karlsruhe, De, Toilet Soap Compositions, vol. 102, No. 22, May 30, 1983; (abstract No. 187086x) Columbus, Ohio US: & JP-A-59 219 399 (Kao Corp.).

Kawabata Akio et al., Production of Hydrogenated Rosin, vol. 390, (C–751) Aug. 23, 1990; & JP-A-02 145 668 (Harima Chem.) Jun. 5, 1990 Abstract.

Solid Detergent Composition vol. 100, (C–693), (Feb. 23, 1990) & JP-A-01 306 500 (Lion Corp.) Nov. 12, 1989 (Cat. X) Patent Abstracts of Japan.

*Primary Examiner*—Thurman K. Page
*Assistant Examiner*—C. Azpuru
*Attorney, Agent, or Firm*—Wegner, Cantor, Mueller & Player

[57] ABSTRACT

A dermatological external agent such as a pharmaceutical, quasi-drug, or cosmetic comprising tetrahydroabietic acid, a salt thereof, and hydrogenated rosin and a salt thereof, formulated therein, has an excellent antibacterial action, is not harmful to the human body, and has an excellent stability.

4 Claims, No Drawings

DERMATOLOGICAL EXTERNAL AGENT

DESCRIPTION

1. Technical Field

The present invention relates to a dermatological external agent, and more specifically, to a dermatological external agent such as a pharmaceutical, quasidrug, or cosmetic which comprises tetrahydroabietic acid and a salt thereof and/or a hydrogenated rosin and a salt thereof formulated therein, and has an excellent antibacterial action but has no adverse affects on the human body, and has an excellent stability.

2. Background Art

It is known in the art that acne (Acne vulgaris) is caused by, for example, an increased secretion of sebum and an infection with bacteria. This infection with bacteria occurs on the comedo formed by a pooling of sebum, to give rise to folliculitis and resulting in pustula or wide-spread induration.

In the prior art, as the compound obtained by an extraction of natural plant components exhibiting an effective antibacterial power against Propionibacterium acnes, which is a Gram-positive anaerobic bacterium regarded as the causative bacterium of acne, picifellinic acid and berberine chloride are known. Although some effects against acne can be observed, with the use of the above-mentioned picifellinic acid and berberine chloride, the effects thereof are not always satisfactory.

DISCLOSURE OF THE INVENTION

Accordingly, an object of the present invention is to develop a dermatological external agent which will effectively inhibit acne.

Other objects and specific features of the present invention will be apparent from the following description.

According to the present invention, there is provided a dermatological external agent comprising at least one compound selected from the group consisting of tetrahydroabietic acid and salts thereof, rosin hydrogenated product and salts thereof, and a carrier which is cosmetically and pharmacologically harmless.

BEST MODE OF CARRYING OUT THE PRESENT INVENTION

The present invention is now described in more detail.

In view of the state of the art as described above, the present inventors made an intensive study into the development of a dermatological external agent which will effectively inhibit acne, and accordingly, found that abietic acid extracted from a plant of the pine family or tetrahydroabietic acid obtained by a hydrogenation of the salt thereof, the salt thereof per se, and a hydrogenated rosin obtained by a hydrogenation of rosin and a salt thereof, are extremely safe and stable and have an extremely strong antibacterial effect against Propionibacterium acnes, to thus accomplish the present invention. There are no known reports on the antibacterial property of tetrahydroabietic acid and salt thereof, or the hydrogenated rosin and salt thereof. The present inventors have accomplished the present invention on the basis of the above finding.

The dermatological external agent of the present invention contains tetrahydroabietic acid and salt thereof, as well as a hydrogenated rosin and salt thereof, as the active component. These compounds may be used alone or in any desired combination thereof.

The present inventors found that tetrahydroabietic acid and salt thereof, as well as a hydrogenated rosin and salt thereof, exhibit a strong antibacterial power against the acne causative bacterium described above, and the present inventors further confirmed that such a strong antibacterial power can be maintained even when formulated into various dermatological external agents. Therefore, the dermatological external agent of the present invention exhibits an excellent preventive-ameliorating effect against Acne vulgaris. Further, the dermatological external agent of the present invention not only exhibits an excellent preventive-ameliorating effect against Acne vulgaris, but also an excellent preventive-ameliorating effect against various bacterial skin diseases.

The content of the compound of the present invention is preferably 0.001 to 10% by weight as the dry residual content of the total amount of the dermatological external agent, more preferably 0.1 to 3% by weight, to thus exhibit a strong antibacterial power against the acne causative bacterium. When the content is less than 0.001% by weight, the effect of the present invention cannot be obtained, and conversely, a content in excess of 10% by weight is disadvantageous to the preparation thereof.

The tetrahydroabietic acid and salt thereof, as well as a hydrogenated rosin and salt thereof, are preferably derived from plants (particularly from plants of the pine family).

As the tetrahydroabietic acid salt and the salt of a hydrogenated rosin, there may be included alkali metal salts such as sodium salt and potassium salt, and organic amine salts such as monoethanolamine salt, diethanolamine salt, and triethanolamine salt of the tetrahydroabietic acid, and alkali metal salts such as sodium salt and potassium salt, and organic amine salts such as monoethanolamine salt, diethanolamine salt, and triethanolamine salt of the hydrogenated rosin, but preferably sodium salts, potassium salts, and triethanolamine salts are employed. At least one or more is suitably chosen and used, from among the above-mentioned tetrahydroabietic acid salts and salts of a hydrogenated rosin, and these can be prepared according to methods generally known in the art.

The tetrahydroabietic acid and hydrogenated rosin can be obtained according to conventional methods by, for example, hydrogenating abietic acid or rosin in the presence of a noble metal catalyst.

In the dermatological external agent of the present invention, in addition to tetrahydroabietic acid and salt thereof, as well as a hydrogenated rosin and salt thereof, oil components and water can be formulated as the carrier or the base for dermatological external agent, depending on the type of the dermatological external agent. Further, if necessary, conventional components generally employed for dermatological external agents in general can be formulated, such as surfactants, humectants, lower alcohols, thickeners, perfumes, antioxidants, chelating agents, dyes, and preservatives.

The dosage form of the dermatological external agent according to the present invention may be as desired, as it can exhibit the preventive-ameliorating against bacterial skin diseases in any dosage form, such as the solution system, the solubilized system, the powder dispersion system, the water-oil two-layer system, or the water-oil-powder three-layer system. Also, the use of the dermatological external agent of the present invention may be as desired, and if can be used widely for pharmaceuticals, quasi-drugs, cosmetics, and toiletry articles. For example, it can be effectively formulated into lotions, milky lotions, creams, packs, hair tonics, hair creams, shampoos, hair rinses, anti-sweat agents, aqueous ointments, oily ointments, soaps, and face washing materials.

EXAMPLES

The present invention is now described in more detail, with reference to Examples, which in no way limit the scope of the present invention. In the following Examples, the formulated amounts are shown in % by weight.

TEST EXAMPLE 1

(Growth Inhibitory Effect Against Gram-Positive Anaerobic Bacterium)

The growth inhibitory effects of tetrahydroabietic acid salts against Acne bacterium, which is a Gram-positive anaerobic bacterium were evaluated as follows.

Using a GAM agar medium produced by Nissui K. K. as the medium, after an adjustment of the pH of the medium to 7.3±0.1, a minimum growth inhibitory concentration (MIC) of sodium tetrahydroabietate and sodium salt of hydrogenated rosin, needed for a Propionibacterium acnes standard strain (ATCC 11827) was measured and evaluated.

As a Control, MIC's of substances generally known to have an antibacterial action (isopropylmethylphenol, berberine chloride, thioxolone, abietic acid) were also measured.

As a result, as shown in Table 1, the sodium tetrahydroabietate and sodium salt of hydrogenated rosin were shown to have a far stronger antibacterial power than other antibacterial substances.

TABLE 1

| Antibacterial substance | MIC (ppm) |
| --- | --- |
| Isopropylmethylphenol | 100 |
| Berberline chloride | 100 |
| Thioxolone | 50 |
| Abietic acid | 20 |
| Tetrahydroabietic acid | 3 |
| Sodium tetrahydroabietate | 5 |
| Sodium salt of hydrogenated rosin | 7 |
| Rosin hydrogenated product | 3 |

TEST EXAMPLE 2

Using an ABCM medium (Eikensha K. K.) as the antibacterial active medium, the medium was heated in an autoclave at a temperature of 115° C. for 15 minutes. A filter paper disc (8 mmφ) impregnated with 0.05 ml of 10% acetone solution of each sample was adhered to an agar plate to which Propionibacterium avidum, ATCC 25577 was previously inoculated and dispersed thereon, and anaerobically cultured at 37° C. for 3 days. The diameter of the transparent band (Propionibacterium avidum growth inhibitory band) formed around the filter paper upon completion of the culturing was measured, and the antibacterial power determined therefrom.

The test results are shown in Table 2.

TABLE 2

| Substance name | Inhibitory band diameter (mm) |
| --- | --- |
| Abietic acid | 15 |
| Tetrahydroabietic acid | 18 |
| Sodium tetrahydroabietate | 17 |

When the same tests were conducted for the hydrogenated rosin and sodium salt of the hydrogenated rosin, as the substance shown in Table 2, the same results as shown in Table 2 were obtained.

The dermatological external agents in all of the Examples exhibited excellent preventing-ameliorating effects against various bacterial dermatological diseases such as Acne vulgaris, etc.

EXAMPLE 1: Cosmetic Lotion

| Formulated components | % |
| --- | --- |
| (1) Sodium tetrahydroabietate | 0.2 |
| (2) Glycerol | 2.0 |
| (3) 1,3-Butylene glycol | 2.0 |
| (4) Sodium citrate | 0.1 |
| (5) Ethanol | 10.0 |
| (6) Polyoxyethylene (15) oleyl ether | 0.5 |
| (7) Para-hydroxybenzoic acid ester | 0.1 |
| (8) Purified water | Balance |
| (Preparation method) | |

The above components (1), (5), (6) and (7) were dissolved by mixing at room temperature, and the mixture was added, while stirring, to the components (2), (3), (4) and (8) dissolved by mixing similarly at room temperature, to thus obtain a cosmetic lotion.

COMPARATIVE EXAMPLE 1: Cosmetic Lotion

A cosmetic lotion was obtained in the same manner as in Example 1, except that the sodium tetrahydroabietinate of the component (1) of the lotion of Example 1 was not contained therein.

The antibacterial effects of the lotions in Example 1 and the comparative Example 1 against Propionibacterium acnes were measured as described below.

Namely, using a GAM agar medium produced by Nissui K. K. as the medium, after adjusting the pH to 7.3±0.1, the medium was heated in an autoclave at a temperature of 115° C. for 15 minutes to obtain a plate agar. An amount of 0.05 ml of a sample was taken on a filter with a diameter of 8 mm, adhered to the GAM agar medium to which a Propionibacterium acnes standard strain (ATCC 11827) was previously inoculated and dispersed thereon, anaerobically cultured at 37° C. for 3 days. The diameter of the transparent band (Propionibacterium acnes growth inhibitory band) formed around the filter paper upon completion of the culturing was measured, and the antibacterial power determined therefrom. The results are shown in Table 3.

TABLE 3

| | Example 1 | Comparative Example 1 |
| --- | --- | --- |
| Growth inhibitory band (mm) | 14 | 9 |

As apparent from the results in Table 3, Example 1 having sodium tetrahydroabietate formulated therein has a larger growth inhibitory band diameter than Comparative Example 1, thus indicating that it has a stronger antibacterial power.

EXAMPLE 2: Cleansing Foam

| Formulated components | % |
| --- | --- |
| (1) Potassium tetrahydroabietate | 0.5 |
| (2) Glycerol | 18.0 |
| (3) Palmitic acid | 10.0 |
| (4) Stearic acid | 10.0 |
| (5) Myristic acid | 12.0 |
| (6) Lauric acid | 4.0 |
| (7) Oleyl alcohol | 1.0 |
| (8) Potassium hydroxide | 6.0 |
| (9) Purified water | Balance |

(Preparation method)

To the above component (9) was added the component (8), the mixture was heated, the component (2) was added thereto, and the mixture immediately heated to 70° C., followed by a gradual addition of the previously heated and melted components (1), (3), (4), (5), (6) and (7) while stirring. After completion of the addition, the temperature was maintained for a while at 70° C., to complete the neutralization reaction, followed by cooling to thus obtain a cleansing foam.

EXAMPLE 3: Acne Cream

| Formulated components | % |
| --- | --- |
| (1) Sodium tetrahydroabietate | 0.1 |
| (2) Photosensitizer 201 | 0.003 |
| (3) 1,3-Butylene glycol | 5.0 |
| (4) Beeswax | 2.0 |
| (5) Cetanol | 4.0 |
| (6) Hydrogenated lanolin | 10.0 |
| (7) Squalane | 30.0 |
| (8) Para-hydroxybenzoic acid ester | 0.2 |
| (9) Polyoxyethylene (20) sorbitane monolaurate | 2.0 |
| (10) Purified water | Balance |

(Preparation method)

Preparation Method

To the above component (10) was added the component (3), and the mixture was heated and maintained at 70° C. (aqueous phase portion). the other components were mixed, heated to 70° C. and dissolved (oil phase portion), and the oil phase portion was added to the aqueous phase portion and preliminarily emulsified, followed by a homogeneous emulsification by a homomixer to thus obtain an O/W cream.

EXAMPLE 4: Pack

| Formulated components | % |
| --- | --- |
| (1) Triethanolamine tetrahydroabietate | 1.0 |
| (2) Vinyl acetate resin emulsion | 12.0 |
| (3) Polyvinyl alcohol | 10.0 |
| (4) Olive oil | 3.0 |
| (5) Sorbitol | 5.0 |
| (6) Titanium dioxide | 15.0 |
| (7) Ethanol | 10.0 |
| (8) Para-hydroxybenzoic acid ester | 0.1 |
| (9) Purified water | Balance |

(Preparation method)

Preparation Method

The component (9) was mixed with the component (5), and to the mixture were added the components (6) and (2), and further, the component (3) wetted with a part of the component (7) was added, followed by heating to 70° C. to be dissolved therein. Next, to the remaining part of the component (7) were added the components (1) and (8) followed by mixing, and finally, the component (4) was added and the mixture was cooled to thus obtain a pack.

EXAMPLE 5: Foundation

| Formulated components | % |
| --- | --- |
| (1) Potassium tetrahydroabietate | 0.2 |
| (2) Titanium dioxide | 13.0 |
| (3) Colloidal kaolin | 25.0 |
| (4) Talc | 44.85 |
| (5) Red iron oxide | 0.8 |
| (6) Yellow iron oxide | 2.5 |
| (7) Black iron oxide | 0.1 |
| (8) Liquid paraffin | 8.0 |
| (9) Sorbitane sesquioleate | 3.5 |
| (10) Glycerol | 2.0 |
| (11) Para-hydroxybenzoic acid ester | 0.2 |

(Preparation method)

Preparation Method

The above components (2) to (7) were mixed and crushed by passing through a crushing machine, to an average particle size of 1 to 5 μm, and the mixture was transferred to a high speed blender and mixed with an addition of the component (10). Separately, the components (1), (8), (9) and (11) were mixed to be made homogeneous, and the resultant mixture was added to the above mixture, followed by a further homogeneous mixing. The resultant mixture was treated by a crushing machine, and the particle sizes were made regular by passing through a sieve, followed by compression molding to obtain a cake type foundation.

EXAMPLE 6: Cream

| Formulated components | % |
| --- | --- |
| (1a) Sodium tetrahydroabietate | 0.5 |
| (1b) Hydrogenated rosin sodium salt | 0.5 |
| (2) Liquid paraffin | 10.0 |
| (3) 1,3-Butylene glycol | 5.0 |
| (4) Beeswax | 2.0 |
| (5) Cetanol | 4.0 |
| (6) Hydrogenated lanolin | 2.0 |
| (7) Squalane | 30.0 |
| (8) Para-hydroxybenzoic acid ester | 0.2 |
| (9) Polyoxyethylene (20) sorbitane Monolaurate | 2.0 |
| (10) Purified water | Balance |

(Preparation method)

Preparation Method

To the above component (10) were added the components (1a), (1b) and (3), and the mixture was heated to and maintained at 70° C. (aqueous phase portion). the other components were mixed, heated and dissolved to 70° C. (oil phase portion), and the oil phase portion was added to the aqueous phase portion and preliminarily emulsified, followed by a homogeneous emulsification by a homomixer to thus obtain an O/W cream.

EXAMPLE 7: Milky Lotion

| Formulated components | % |
| --- | --- |
| (1) Potassium tetrahydroabietate | 0.5 |

| Formulated components | % |
| --- | --- |
| (2) Liquid paraffin | 10.0 |
| (3) Petrolatum | 4.0 |
| (4) Stearic acid | 2.0 |
| (5) Cetanol | 1.0 |
| (6) Glycerol monostearate (self-emulsified type) | 2.0 |
| (7) Propylene glycol | 7.0 |
| (8) Purified water | Balance |
| (9) Sodium hydroxide | 0.4 |

(Preparation method)

Preparation Method

The above components (1) to (6) were mixed, heated, dissolved and then maintained at 70° C. (oil phase). The components (7), (8) and (9) were mixed and dissolved, and then heated and maintained at 70° C. (aqueous phase). The oil phase was then added to the aqueous phase, and the mixture homogeneously emulsified by a homomixer and cooled to 30° C. while thoroughly stirring.

EXAMPLE 8: Oily Ointment

| Formulated components | % |
| --- | --- |
| (1) Sodium tetrahydroabietate | 0.5 |
| (2) Shortening oil | 3.0 |
| (3) Petrolatum | 96.5 |

(Preparation method)

Preparation Method

The above components were mixed, heated to 80° C., and gradually cooled.

EXAMPLE 9: Shampoo

| Formulated components | % |
| --- | --- |
| (1) Polyoxyethylene (3) lauryl ether sulfate sodium salt (30% aqueous solution) | 30.0 |
| (2) Lauryl sulfate sodium salt (30% aqueous solution) | 15.0 |
| (3) Ethylene glycol distearate | 3.0 |
| (4) Lauroyl diethanolamide | 2.0 |
| (5) Polyoxyethylene (15) lanolin alcohol | 1.0 |
| (6) Polyoxyethylene (12) lauryl ether | 3.0 |
| (7) Hydrogenated rosin sodium salt | 0.5 |
| (8) Purified water | 46.5 |
| (9) Perfume | q.s. |
| (10) Dye | q.s. |
| (11) Para-hydroxybenzoic acid ester | q.s. |
| (12) UV-ray absorber, sequestering agent | q.s. |

(Preparation method)

Preparation Method

Purified water was heated, and other components were added thereto to be dissolved therein, and after thoroughly stirring, the solution was slowly cooled.

EXAMPLE 10: Anti-Sweat Agent

| | % |
| --- | --- |
| Stock liquid recipe | |
| (1) Aluminum hydroxychloride | 30.0 |
| (2) Silicic anhydride | 5.0 |
| (3) Talc | 1.0 |
| (4) Sodium tetrahydroabietate | 1.0 |
| (5) Isopropyl myristate | 63.0 |
| (6) Perfume | q.s. |
| Filling recipe | |
| (1) Stock liquid | 10.0 |
| (2) Gas | 90.0 |

(Preparation method)

Preparation Method

The stock liquid, after other components were gradually added to isopropyl myristate while stirring, was homogeneously dispersed by a homomixer. Filling was performed by filling the stock liquid in the prescribed amount into a can, and after mounting the valve, filling the prescribed amount of gas.

In the above Examples, the incorporation of a tetrahydroabietic acid salt or a hydrogenated rosin salt alone was shown, but when both were used in combination, an even stronger antibacterial action was exhibited than when they were incorporated alone.

EXAMPLE 11: Cosmetic Lotion

| Formulated components | % |
| --- | --- |
| (1) Tetrahydroabietic acid | 0.5 |
| (2) Glycerol | 2.0 |
| (3) 1,3-Butylene glycol | 2.0 |
| (4) Sodium citrate | 0.1 |
| (5) Ethanol | 10.0 |
| (6) Polyoxyethylene (15) oleyl ether | 0.5 |
| (7) Para-hydroxybenzoic acid ester | 0.1 |
| (8) Purified water | Balance |

(Preparation method)

Preparation Method

The above components (1), (5), (6) and (7) were dissolved by mixing at room temperature, and added into the components (2), (3), (4) and (8) dissolved by mixing similarly at room temperature while stirring, to thus obtain a cosmetic lotion.

COMPARATIVE EXAMPLE 2: Lotion

A cosmetic lotion was obtained in exactly the same manner as in Example 11, except that the tetrahydroabietic acid of the component (1) in Example 11 was not contained therein.

The antibacterial effects of the lotions in Example 11 and Comparative Example 2 against Propionibacterium acnes were measured as described below.

Using a GAM agar medium produced by Nissui K. K., as the medium, and after adjusting the pH thereof to 7.3±0.1, the medium was heated in an autoclave at a temperature of 115° C. for 15 minutes to obtain a plate agar. An amount of 0.05 ml of a sample was taken onto a filter with a diameter of 8 mm, adhered to the GAM agar medium to which Propionibacterium acnes standard strain (ATCC 11827) was previously inoculated and dispersed thereon, and anaerobically cultured at 37° C. for 3 days. The diameter of the transparent band (Propionibacterium acnes growth inhibitory band) formed around the filter paper on completion of the culturing was measured, and the antibacterial power determined therefrom. The results are shown in Table 4.

TABLE 4

|  | Example 11 | Comparative Example 2 |
|---|---|---|
| Growth inhibitory band (mm) | 14 | 9 |

As apparent from the results in Table 4, Example 11 having tetrahydroabietic acid formulated therein has a larger growth inhibitory band diameter than Comparative Example 2, thus indicating that it has a stronger antibacterial power.

EXAMPLE 12: Acne Cream

| Formulated components | % |
|---|---|
| (1) Tetrahydroabietic acid | 0.5 |
| (2) Photosensitizer 201 (Nippon Kanko Shikiso K.K.) | 0.003 |
| (3) 1,3-Butylene glycol | 5.0 |
| (4) Beeswax | 2.0 |
| (5) Cetanol | 4.0 |
| (6) Hydrogenated lanolin | 10.0 |
| (7) Squalane | 30.0 |
| (8) Para-oxybenzoic acid ester | 0.2 |
| (9) Polyoxyethylene (20) sorbitane monolaurate | 2.0 |
| (10) Purified water | Balance |

(Preparation method)

Preparation Method

To the above component (10) was added the component (3), and the mixture was heated and maintained at 70° C. (aqueous phase portion). The other components were mixed, heated and dissolved to 70° C. (oil phase portion), and the oil phase portion was added to the aqueous phase portion and preliminarily emulsified, followed by a homogeneous emulsification by a homomixer, to thus obtain an O/W cream.

EXAMPLE 13: Pack

| Formulated components | % |
|---|---|
| (1) Tetrahydroabietic acid | 3.0 |
| (2) Vinyl acetate resin emulsion | 12.0 |
| (3) Polyvinyl alcohol | 10.0 |
| (4) Olive oil | 3.0 |
| (5) Sorbitol | 5.0 |
| (6) Titanium dioxide | 15.0 |
| (7) Ethanol | 10.0 |
| (8) Para-hydroxybenzoic acid ester | 0.1 |
| (9) Purified water | Balance |

(Preparation method)

Preparation Method

The component (9) was mixed with the component (5), and to the mixture were added the components (6) and (2), and further, the component (3) wetted with a part of the component (7) was added, followed by heating to 70° C. to be dissolved therein. Next, to the remaining part of the component (7) were added the components (1) and (8), followed by mixing, and finally the component (4) was added and the mixture was cooled, to thus obtain a pack.

EXAMPLE 14: Foundation

| Formulated components | % |
|---|---|
| (1) Tetrahydroabietic acid | 0.2 |
| (2) Titanium dioxide | 13.0 |
| (3) Colloidal kaolin | 25.0 |
| (4) Talc | 44.85 |
| (5) Red iron oxide | 0.8 |
| (6) Yellow iron oxide | 2.5 |
| (7) Black iron oxide | 0.1 |
| (8) Liquid paraffin | 8.0 |
| (9) Sorbitane sesquioleate | 3.5 |
| (10) Glycerol | 2.0 |
| (11) Para-hydroxybenzoic acid ester | 0.2 |

(Preparation method)

Preparation Method

The above components (2) to (7) were mixed and crushed by passing through a grinding machine to an average particle size of 1 to 5 μm, and the mixture was transferred to a high speed blender and mixed with addition of the component (10). Separately, the components (1), (8), (9) and (11) were mixed to be made homogeneous, and the resultant mixture was added to the above mixture, followed by a further homogeneous mixing. The resultant mixture was treated by a crushing machine, and the particle sizes were made regular by passing through a sieve, followed by compression molding to obtain a cake type foundation.

EXAMPLE 15: Cream

| Formulated components | % |
|---|---|
| (1) Tetrahydroabietic acid | 1.0 |
| (2) Sodium tetrahydroabietate | 1.0 |
| (3) Liquid paraffin | 10.0 |
| (4) 1,3-Butylene glycol | 5.0 |
| (5) Beeswax | 2.0 |
| (6) Cetanol | 4.0 |
| (7) Hydrogenated lanolin | 2.0 |
| (8) Squalene | 30.0 |
| (9) Para-hydroxy benzoic acid ester | 0.2 |
| (10) Polyoxyethylene (20) sorbitane monolaurate | 2.0 |
| (11) Purified water | Balance |

(Preparation method)

Preparation Method

To the above component (11) were added the components (2) and (4), and the mixture was heated to and maintained at 70° C. (aqueous phase portion). The other components were mixed, heated and dissolved to 70° C. (oil phase portion), and the oil phase portion was added to the aqueous phase portion and preliminarily emulsified, followed by a homogeneous emulsification by a homomixer, to thus obtain an O/W cream.

EXAMPLE 16: Milky Lotion

| Formulated components | % |
|---|---|
| (1) Tetrahydroabietic acid | 0.5 |
| (2) Liquid paraffin | 10.0 |
| (3) Petrolatum | 4.0 |
| (4) Stearic acid | 2.0 |
| (5) Cetanol | 1.0 |
| (6) Glycerol monostearate (self-emulsified type) | 2.0 |
| (7) Propylene glycol | 7.0 |
| (8) Purified water | Balance |

| Formulated components | % |
| --- | --- |
| (9) Sodium hydroxide | 0.4 |
| (Preparation method) | |

Preparation Method

The above components (1) to (6) were mixed, heated, dissolved, and then maintained at 70° C. (oil phase). The components (7) to (9) were mixed and dissolved, and then heated and maintained at 70° C. (aqueous phase). The oil phase was added to the aqueous phase, and the mixture then homogeneously emulsified by a homomixer and cooled to 30° C. while thoroughly stirring.

EXAMPLE 17: Oily Ointment

| Formulated components | % |
| --- | --- |
| (1) Tetrahydroabietic acid | 0.5 |
| (2) Shortening oil | 3.0 |
| (3) Petrolatum | 96.5 |

Preparation Method

The above components were mixed, heated to 80° C., and gradually cooled.

EXAMPLE 18: Shampoo

| Formulated components | % |
| --- | --- |
| (1) Polyoxyethylene (3) lauryl ether sulfate sodium salt (30% aqueous solution) | 30.0 |
| (2) Lauryl sulfate sodium salt (30% aqueous solution) | 15.0 |
| (3) Ethylene glycol distearate | 3.0 |
| (4) Lauroyl diethanolamide | 2.0 |
| (5) Polyoxyethylene (15) lanolin alcohol | 1.0 |
| (6) Polyoxyethylene (12) lauryl ether | 3.0 |
| (7) Rosin hydrogenated product | 0.5 |
| (8) Purified water | 46.5 |
| (9) Perfume | q.s. |
| (10) Dye | q.s. |
| (11) Para-hydroxybenzoic acid ester | q.s. |
| (12) UV-ray absorber, sequestering agent | q.s. |
| (Preparation method) | |

Preparation Method

Purified water was heated, and other components were added thereto to be dissolved therein, and after a thorough stirring, the solution was slowly cooled.

| | % |
| --- | --- |
| .Stock liquid recipe | |
| (1) Aluminum hydroxychloride | 30.0 |
| (2) Silicic anhydride | 5.0 |
| (3) Talc | 1.0 |
| (4) Tetrahydroabietate acid | 1.0 |
| (5) Isopropyl myristate | 63.0 |
| (6) Perfume | q.s. |
| .Filling recipe | |
| (1) Stock liquid | 10.0 |
| (2) Gas | 90.0 |
| (Preparation method) | |

Preparation Method

The stock liquid, after other components were gradually added to isopropyl myrystate while stirring, was homogeneously dispersed by a homomixer. Filling was performed by filling the stock liquid in the prescribed amount into a can, and after mounting the valve, filling the prescribed amount of gas.

UTILIZABILITY IN INDUSTRY

The present invention contains tetrahydroabietic acid and salt thereof and/or hydrogenated rosin and salt thereof in a dermatological external agent, and therefore, is extremely effective against various bacterial dermatological diseases such as Acne vulgaris, etc., and a dermatological external agent which is very safe and stable is obtained.

We claim:

1. A method for inhibiting bacterial dermatological diseases comprising administering to a patient in need thereof a dermatological external agent comprising an antibacterial effective amount of at leas tone compound selected from the group consisting of tetrahydroabietic acid, salts thereof, hydrogenated rosin and salts thereof, and a cosmetically and pharmacologically acceptable carrier.

2. A method according to claim 1, wherein the antibacterial effective amount of the at least one compound is 0.001 to 10% by weight.

3. A method according to claim 1, wherein the tetrahydroabietic acid salts are alkali salts and organic amine salts of tetrahydroabietinic acid.

4. A method according to claim 1, wherein the hydrogenated rosin salts are alkali metal salts and organic amine salts of a hydrogenated rosin.

* * * * *